United States Patent
Miyamoto et al.

(10) Patent No.: US 6,348,613 B2
(45) Date of Patent: Feb. 19, 2002

(54) PROCESS FOR PRODUCING DIARYL CARBONATE

(75) Inventors: Masaaki Miyamoto; Narutoshi Hyoudou, both of Kitakyushu (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/748,766

(22) Filed: Dec. 26, 2000

(30) Foreign Application Priority Data

Dec. 28, 1999 (JP) .......................................... 11-374300

(51) Int. Cl.$^7$ ............................................... C07C 69/96
(52) U.S. Cl. ..................................................... 558/274
(58) Field of Search ......................................... 558/274

(56) References Cited

U.S. PATENT DOCUMENTS

| | | | |
|---|---|---|---|
| 4,012,406 A | 3/1977 | Buysch et al. | 260/463 |
| 4,774,070 A | 9/1988 | Itoh et al. | 423/502 |

FOREIGN PATENT DOCUMENTS

| | | | |
|---|---|---|---|
| JP | 9-278714 | 10/1997 | 69/96 |
| JP | 10-182104 | 7/1998 | 7/4 |

OTHER PUBLICATIONS

Process Flowsheet; New Chlorine Source: Byproduct Hydrochloric Sep. 14, 1964, Chemical Engineering pp. 172–174.

*Primary Examiner*—Joseph K. McKane
*Assistant Examiner*—Joseph Murray
(74) *Attorney, Agent, or Firm*—David G. Conlin; John B. Alexander; Dike, Bronstein, Roberts & Cushman (57) ABSTRACT

A process for producing diaryl carbonate of the present invention comprises steps of:

(1) a diaryl carbonate production step of subjecting an aromatic monohydroxy compound and phosgene to condensation reaction at a temperature of 80 to 180° C. in the presence of an aromatic nitrogen-containing heterocyclic compound catalyst to obtain the diaryl carbonate;

(2) a purification step of removing impurities from a hydrogen chloride gas by-produced upon the condensation reaction;

(3) a chlorine recovery step of recovering chlorine usable for the production of phosgene from the purified hydrogen chloride gas; and (4) a phosgene production step of reacting the recovered chlorine with carbon monoxide to obtain phosgene usable in the diaryl carbonate production step.

9 Claims, 6 Drawing Sheets

PROCESS FOR PRODUCING DIARYL CARBONATE

BACKGROUND OF THE INVENTION

The present invention relates to a process for producing diaryl carbonate, and more particularly, to a process for producing diaryl carbonate, in which hydrogen chloride by-produced by phosgene method is converted into chlorine and then is used in the production of phosgene.

Large amounts of diaryl carbonates have been used as raw materials for producing aromatic polycarbonates by subjecting the diaryl carbonate to transesterification with bisphenol A. As the method for the production of diaryl carbonate, there is well known such a method comprising producing diaryl carbonate from dialkyl carbonate, and recovering and recycling by-produced alkyl alcohol. However, in this method, there are caused various inconveniences such as difficult separation of respective reaction products, discoloration of aromatic polycarbonates obtained from the diaryl carbonate due to impurities by-produced upon the transesterification reaction, production of undesired cross-linked aromatic polycarbonates or the like. Therefore, it has been required to improve these methods.

On the other hand, as methods of producing diaryl carbonate from phosgene, there are known many methods comprising using a homogeneous catalyst or a heterogeneous catalyst. However, in these phosgene methods, many unsolved problems still remain, for example, such that by-produced aryl salicylate has a boiling point which is extremely close to that of the aimed diaryl carbonate, a catalyst recovery step is required when using the homogeneous catalyst, or metal components is eluted when using the heterogeneous catalyst. Also, in a method of using an activated carbon catalyst, although this method is free from the problem as to elusion of metal components, it is difficult to achieve an industrially useful reaction rate.

It is also known to produce diaryl carbonate by reacting an aromatic monohydroxy compound with phosgene. For example, in U.S. Pat. No. 2,837,555, there has been proposed the method of conducting a solvent-free condensation reaction in the presence of halogenated tetramethyl ammonium as a catalyst. However, in this method, the use of a relatively large amount of the catalyst and a relatively high reaction temperature ranging from 180 to 215° C. are required to achieve an economically useful reaction rate. Therefore, the method tends to cause the decomposition of thermally unstable halogenated tetramethyl ammonium. Besides, in this method, the phosgene is consumed in such a large amount far exceeding the stoichiometric amount thereof.

In Japanese Patent Publication (KOKOKU) No. 58-50977 (1983), there has been proposed the method of producing diaryl carbonate (diphenyl carbonate) by reacting 2 moles of an aromatic monohydroxy compound (phenol) with one mole of phosgene at a temperature of 40 to 180° C. using an aromatic nitrogen-containing heterocyclic compound as a catalyst optionally in a solvent, while eliminating hydrogen chloride from the reaction system. In this method, the reaction temperature is lower than that used in the above U.S. Patent, and the reaction rate is higher by two or more times than that described in the above U.S. Patent.

Thus, the method as described in Japanese Patent Publication (KOKOKU) No. 58-50977(1983) is industrially advantageous for the above-described reasons. However, in this method, the production rate of diphenyl carbonate upon the reaction between phenyl chloroformate as an intermediate product of the diphenyl carbonate and phenol, is low as compared to the production rate of the phenyl chloroformate. As a result, after completion of the reaction, a small amount of phenyl chloroformate still remains in the reaction system together with the diphenyl carbonate. The residual phenyl chloroformate adversely affects the quality of aromatic polycarbonate produced from the diaryl carbonate, as described above.

In order to industrially produce a high-quality polycarbonate, there has been studied a method of producing high-quality diaryl carbonate containing no aryl chloroformate. It is known that this object can be achieved by the following two-stage process. That is, in the process for producing diaryl carbonate comprising reacting the aromatic monohydroxy compound with phosgene in the presence of the aromatic nitrogen-containing heterocyclic compound, the phosgene is used in an amount of 0.44 to 0.5 equivalent based on one equivalent of the aromatic monohydroxy compound so that diary carbonate and aryl chloroformate are produced in such an equivalent amount less than that of unreacted aromatic monohydroxy compound; and then the aryl chloroformate and aromatic monohydroxy compound contained in a reaction solution obtained from the above step, are then subjected to dehydrochlorination reaction to produce diaryl carbonate (refer to Japanese Patent Application Laid-Open (KOKAI) No. 9-278714 (1997)). Further, in the above KOKAI, it is simply described that hydrochloric acid by-produced upon the above reaction is reused in plant, but the purpose of use of the by-product is not clearly specified therein.

On the contrary, the diaryl carbonate production process of the present invention, constitutes a closed cycle capable of reusing the by-product, and more specifically, it is to provide an ideal process in which the by-produced hydrogen chloride is reused for the production of phosgene.

Thus, in the process for producing diaryl carbonate by reacting the aromatic monohydroxy compound with phosgene using the aromatic nitrogen-containing heterocyclic compound as a catalyst, an industrially advantageous high-conversion ratio can be achieved; no salicylate-based impurities are produced unlike conventional methods of producing diaryl carbonate from dialkyl carbonate; and the aimed product can be readily separated from the by-produced monomers, so that it is possible to obtain diaryl carbonate having an extremely high purity at a high yield.

Hitherto, there have been conducted many studies as to methods for converting hydrogen chloride into chlorine. In particular, a large number of patent applications concerning oxidation reactions using a chromium oxide catalyst have been filed (refer to Japanese Patent Publication (KOKOKU) Nos. 6-15402(1994), 5-3402(1993), 5-3403(1993), 5-3405 (1993), 5-3406(1993), 5-69042(1993) and 6-17203(1994)). Recently, many patent applications concerning oxidation reactions using a ruthenium oxide catalyst have also been filed (refer to Japanese Patent Application Laid-Open (KOKAI) Nos. 9-67103(1997), 10-194705(1998), 10-182104(1998), 10-338502(1998), 11-180701(1999) and 2000-34105).

However, in these prior arts, although the methods of converting hydrogen chloride into chlorine are described, there is neither taught nor suggested purposes of use of the converted chlorine, especially there are no prior documents teaching all steps of from the production of phosgene from the recovered chlorine to the production of diaryl carbonate.

SUMMARY OF THE INVENTION

An object of the present invention is to provide a process for producing diaryl carbonate by reacting an aromatic monohydroxy compound with phosgene using a catalyst comprising an aromatic nitrogen-containing heterocyclic compound, in which the diaryl carbonate can be produced at a high conversion ratio in an industrially advantageous manner, the by-produced hydrogen chloride is converted into chlorine, and the converted chlorine is used in phosgene production process.

As a result of the present inventors' earnest studies concerning the purity of purified hydrogen chloride required for the reaction for converting hydrogen chloride into chlorine, the purity of recovered chlorine required for reusing it for the production of phosgene, the purity of the obtained phosgene required for the reaction with the aromatic monohydroxy compound, the concentration of impurities required for achieving the closed cycle process, and the position to which the impurities are purged off, the present invention has been attained based on the finding.

That is, in a first aspect of the present invention, there is provided a process for producing diaryl carbonate, comprising steps of:

(1) a diaryl carbonate production step of subjecting an aromatic monohydroxy compound and phosgene to condensation reaction at a temperature of 80 to 180° C. in the presence of an aromatic nitrogen-containing heterocyclic compound catalyst to obtain the diaryl carbonate;

(2) a purification step of removing impurities from a hydrogen chloride gas by-produced upon the condensation reaction;

(3) a chlorine recovery step of recovering chlorine usable for the production of phosgene from the purified hydrogen chloride gas; and (4) a phosgene production step of reacting the recovered chlorine with carbon monoxide to obtain phosgene usable in the diaryl carbonate production step.

In a second aspect of the present invention, there is provided the process for producing diaryl carbonate, having the following features.

(a) In the chlorine recovery step, the hydrogen chloride gas is subjected to oxidation reaction using oxygen at a temperature of 300 to 500° C. in the presence of a chromium oxide catalyst under such a condition that the oxygen is used in an amount of not less than 0.25 mole based on one mole of the hydrogen chloride.

(b) After removing hydrogen chloride and water from a crude chlorine gas obtained by the oxidation reaction, the resultant chlorine gas is compressed and liquefied to obtain chlorine usable in the phosgene production step, and after recovering chlorine gas from unliquefied chlorine gas, the recovered chlorine gas is recycled to said compression and liquefaction step.

(c) A part of an oxygen-containing gas obtained after removing chlorine from the unliquefied gas, is discharged as an off-gas, and the remainder of the oxygen-containing gas is recycled to the oxidation reaction.

(d) In another chlorine recovery step, the purified hydrogen chloride gas is absorbed into water to prepare an aqueous hydrogen chloride solution having a predetermined concentration, and the aqueous hydrogen chloride solution is subjected to electrolysis.

(e) After removing water from a crude chlorine gas obtained by the electrolysis, the resultant chlorine gas is compressed and liquefied to obtain chlorine usable in the phosgene production step, whereupon a part of a circulating catholyte in an electrolytic cell is used for absorbing the purified hydrogen chloride gas thereinto.

(f) In other chlorine recovery step, the hydrogen chloride gas is subjected to oxidation reaction using oxygen at a temperature of 200 to 400° C. in the presence of a ruthenium oxide catalyst under such a condition that the oxygen is used in an amount of not less than 0.25 mole based on one mole of the hydrogen chloride.

(g) After removing hydrogen chloride and water from a crude chlorine gas obtained by the above-mentioned oxidation reaction, the resultant chlorine gas is compressed and liquefied to obtain chlorine usable in the phosgene production step, and a part of the unliquefied oxygen-containing gas is discharged as an off-gas, and the remainder of the unliquefied oxygen-containing gas is recycled to the oxidation reaction.

(h) In the phosgene production step, a crude phosgene gas obtained by reacting chlorine with carbon monoxide is cooled and liquefied to obtain phosgene usable in the diaryl carbonate production step, and the unliquefied gas is discharged as an off-gas after completely decomposing phosgene.

DETAILED DESCRIPTION OF THE INVENTION

The respective steps of the process according to the present invention are shown by the following chemical formulae.

(1) Diaryl carbonate production step:

PCF+PhOH→DPC+HCl

(2) Chlorine recovery step (oxidation reaction):

(3) Chlorine recovery step (Electrolysis):

(4) Phosgene production step:

wherein PhOH represents phenol; PCF represents phenyl chloroformate; and DPC represents diphenyl carbonate.

The present invention will be described in detail below.

(1) Diaryl Carbonate Production Step

Catalyst:

The catalysts used in the condensation reaction between the aromatic monohydroxy compound and phosgene, are aromatic nitrogen-containing heterocyclic compounds containing a 6-membered ring or a 5-membered ring. These rings may contain hetero atoms other than nitrogen such as sulfur, oxygen and second nitrogen. The heterocyclic group may be condensed with other aromatic heterocyclic group or aromatic carbocyclic group to form a condensed ring.

Examples of the catalysts may include pyridine, quinolines, isoquinoline, picolines, acridine, pyrazine, pyrimidine, imidazole, 2-methyl imidazole, 2-methoxy pyridine, 2-hydroxy pyridine or the like. Among these compounds, pyridine, α-picoline, β- and γ- mixed picoline, isoquinoline, 2-hydroxy pyridine and imidazole are preferred. In addition, polymers of the above-described compounds such as polyvinyl pyridine may also be used as the catalyst.

The amount of the catalyst used is usually 0.1 to 10 mol %, preferably 0.5 to 5 mol % based on the aromatic monohydroxy compound as the base material. The catalyst is rapidly converted into a corresponding hydrochloride in the reaction mixture. Accordingly, the same reactivity and selectivity as obtained by the use of the above-described compounds can also be achieved by using chlorides of these compounds as the catalyst. Similarly, strong acid salts of these compounds such as bromates, sulfates and nitrates may also be used as the catalyst. Furthermore, weak acid salts of these compounds such as formates, acetates, phosphates, caproates and pivalates are readily converted into hydrochlorides and, therefore, may also be used instead of the above catalysts.

Aromatic monohydroxy compound:

Examples of the aromatic monohydroxy compounds used in the present invention may include phenol, cresol (and isomers thereof), isopropyl phenol (and isomers thereof); and halogenated phenols or alkoxy phenols such as chlorophenol (and isomers thereof) and methoxy phenol (and isomers thereof). Further, there may also be used heterocyclic monohydroxy compounds having a 5- or 6-membered ring which may be condensed or substituted with an aromatic ring group, for example, there may be used 4-hydroxy quinoline. Among these aromatic monohydroxy compounds, phenol is especially preferred.

Condensation reaction:

The aromatic monohydroxy compound and phosgene are reacted with each other at a temperature of 80 to 180° C., preferably 120 to 160° C. in the presence of the aromatic nitrogen-containing heterocyclic compound as catalyst. When the reaction temperature is too high, the amount of by-products is increased. When the reaction temperature is too low, the reaction rate becomes too low. The condensation reaction may be usually conducted by introducing a phosgene gas into a molten mixture of the aromatic monohydroxy compound and the aromatic nitrogen-containing heterocyclic compound as catalyst, while stirring the mixture.

The amount of phosgene introduced is not more than one mole, preferably 0.4 to 0.5 mole based on one mole of the aromatic monohydroxy compound. When the amount of phosgene introduced is adjusted to not more than the stoichiometric amount thereof, i.e., 0.5 mole, an unreacted aromatic monohydroxy compound necessarily remains, thereby promoting the diaryl carbonate production reaction between aryl chloroformate as an intermediate product and the unreacted aromatic monohydroxy compound. As a result, it becomes possible to obtain a reaction mixture containing no aryl chloroformate, which adversely affects the production of colorless polycarbonate. In this case, if required, after the introduction of phosgene, a nitrogen gas may be blown into the reaction mixture to remove hydrogen chloride by-produced in the condensation reaction, out of the reaction system, thereby further promoting the above diaryl carbonate production reaction.

(2) Purification Step

Hydrogen chloride:

The hydrogen chloride gas by-produced in the condensation reaction between the aromatic monohydroxy compound and phosgene, contains in addition to unreacted aromatic monohydroxy compound, various organic impurities such as by-products or side reaction products, e.g., bromine-substituted compounds or carbon tetrachloride. Therefore, in order to effectively use the hydrogen chloride gas in the subsequent chlorine recovery step without any troubles, it is required to remove these impurities therefrom. As method for removing the impurities from the hydrogen chloride gas, there may be suitably used the method of contacting the hydrogen chloride gas with an adsorbent such as activated carbon to remove the organic impurities therefrom. In the case where activated carbon is used, the hydrogen chloride gas is passed through a column packed with activated carbon having a large pore volume, so that it is possible to completely remove the organic impurities from the gas and obtain a highly-purified hydrogen chloride gas. The above adsorption treatment is preferably conducted at a low temperature, namely at a temperature of usually not more than 80° C., preferably 10 to 40° C. Further, in the above adsorption treatment, the hydrogen chloride gas is suitably introduced at a low flow rate in order to achieve a good adsorption efficiency. The flow rate of the hydrogen chloride gas is usually about several hundreds per hour, preferably not more than 200 per hour (calculated as SV (hourly space velocity)).

As other methods of reducing the content of the organic impurities in the hydrogen chloride gas, there may be used a liquefaction-distillation method, a washing method using a high-boiling solvent, a low-temperature separation method or combinations of these methods.

(3) Chlorine Recovery Step

Chlorine:

Various methods are applicable in order to obtain chlorine usable in the subsequent phosgene production step from the above purified hydrogen chloride gas. In general, there may be used an oxidation reaction method using a chromium oxide catalyst and an electrolysis method.

Further, recently, there has been proposed such an oxidation reaction method using a ruthenium oxide catalyst, which has a high catalytic activity and, therefore, can catalyze the oxidation reaction at a lower temperature even when used in a small amount.

(a) Oxidation Reaction:

The oxidation reaction of hydrogen chloride using a chromium oxide catalyst is conducted by contacting the purified hydrogen chloride gas and an oxygen gas with a solid catalyst at a temperature of 300 to 500° C. As the contact method, there may be used any of fixed bed-type, fluidized bed-type and moving bed-type methods. The amount of oxygen used for the oxidation reaction of hydrogen chloride is not less than 0.25 mole based on one mole of the hydrogen chloride. When the amount of oxygen used is too small, it is not possible to maintain the catalyst under an oxygen atmosphere, resulting in deteriorated activity of the catalyst. However, when the amount of oxygen used is too large, additional facilities are required for reusing the excess amount of oxygen. Therefore, the amount of oxygen used for the oxidation reaction of hydrogen chloride is usually in the range of about 0.3 to 1 mole based on one mole of the hydrogen chloride.

The crude chlorine gas obtained by the oxidation reaction contains unreacted hydrogen chloride and oxygen in addition to water by-produced in the oxidation reaction. In consequence, after the unreacted hydrogen chloride is recovered in water from the crude chlorine gas, the resultant chlorine gas is dehydrated with sulfuric acid, and then compressed and liquefied, thereby obtaining liquefied chlorine having a high purity which is usable in the phosgene production step. Upon practical use, after the liquefied chlorine is vaporized, the obtained chlorine gas is supplied to the phosgene production step described hereinafter. On the other hand, the unliquefied gas contains a considerable amount of chlorine in addition to oxygen. The chlorine contained in the unliquefied gas is usually recovered by absorbing it into carbon tetrachloride or recovered by pressure-swing-adsorption (PSA) separation method. The recovered chlorine is vaporized and then recycled to the above compression and liquefaction step.

On the other hand, the residual oxygen-containing gas obtained after recovering chlorine from the unliquefied gas is treated, for example, with a sodium sulfite solution to absorb carbon tetrachloride entrained on the gas thereinto. Then, a part of the resultant detoxified gas containing oxygen at a high concentration is discharged into atmosphere as an off-gas, and the remainder of the gas is recycled to the oxidation reaction step for reuse.

The ruthenium oxide catalyst can exhibit a high catalytic activity when used in the oxidation reaction of hydrogen chloride. Therefore, by using such a ruthenium oxide catalyst, the oxidation reaction can be conducted in the same manner as that using the above chromium oxide catalyst except that the reaction temperature is adjusted to the range of 200 to 400° C.

(b) Electrolysis:

Upon electrolysis of hydrogen chloride, the purified hydrogen chloride gas is absorbed into water to prepare an aqueous hydrogen chloride solution having a predetermined concentration, and then the aqueous hydrogen chloride solution is subjected to electrolysis. In order to suitably conduct the electrolysis, the concentration of hydrogen chloride in the aqueous solution is usually 10 to 40% by weight, preferably 15 to 30% by weight. When the hydrogen chloride concentration is too high, the electric conductivity of the aqueous solution may be lowered, so that the electrolytic cell voltage is disadvantageously increased. On the other hand, when the hydrogen chloride concentration is too low, there may be caused disadvantages such as increase in consumption of graphite electrodes and amount of oxygen generated. As a result of the electrolysis, a crude hydrogen gas is collected at the cathode, and a crude chlorine gas is collected at the anode.

The crude chlorine gas generated in an anode chamber of the electrolytic cell contains water entrained thereon and a small amount of hydrogen chloride. Therefore, when the crude chlorine gas is cooled to remove condensed water, the hydrogen chloride is simultaneously condensed and removed in the form of diluted hydrochloric acid. After the removal of water, the chlorine gas is compressed and liquefied to obtain liquefied chlorine usable in the phosgene production step. Upon practical use, the liquefied chlorine is vaporized, and the obtained chlorine gas is fed to the phosgene production step described hereinafter. The diluted hydrochloric acid obtained above is reused to prepare the aqueous hydrogen chloride solution having a predetermined concentration as an electrolyte.

The crude hydrogen gas generated in a cathode chamber of the electrolytic cell contains water entrained thereon and a small amount of hydrogen chloride. Therefore, when the crude hydrogen gas is cooled to remove condensed water, a part of the hydrogen chloride is simultaneously condensed and removed in the form of diluted hydrochloric acid. The diluted hydrochloric acid is reused to prepare the aqueous hydrogen chloride solution having a predetermined concentration as an electrolyte. On the other hand, uncondensed hydrogen chloride contained in the crude hydrogen gas is neutralized and removed, thereby obtaining a purified hydrogen gas.

In the above electrolysis, it is preferred that a part of a circulating catholyte in the electrolytic cell is used to absorb the purified hydrogen chloride gas thereinto. The amount of the catholyte used for the above purpose may be appropriately determined so as to obtain the aqueous hydrogen chloride solution having the predetermined concentration in view of the amount of hydrochloric acid used for preparing the aqueous solution.

(4) Phosgene Production Step

Phosgene:

The recovered chlorine and carbon monoxide are reacted with each other by passing a mixed gas of the recovered chlorine and carbon monoxide through a column packed with activated carbon, thereby obtaining phosgene usable in the diaryl carbonate production step. As a result of the reaction, the maximum reaction temperature reaches 300 to 400° C. Therefore, the gas temperature at an outlet of the reactor is controlled to not more than 100° C. by external cooling using a coolant. The crude phosgene gas obtained by the reaction is cooled to a temperature of not more than 0° C. by a heat exchanger, condensed and stored in the form of liquefied phosgene usable in the diaryl carbonate production step. Upon practical use, after the liquefied phosgene is vaporized, the obtained phosgene gas is fed to the diaryl carbonate production step. Thus, in many cases, phosgene is usually temporarily stored as liquefied phosgene. Alternatively, gaseous phosgene may be directly supplied without liquefaction thereof together with carbon monoxide, to the diaryl carbonate production step where the carbon monoxide may be treated as an off-gas. On the other hand, the unliquefied gas is discharged as an off-gas into atmosphere after completely decomposing phosgene using, for example, an aqueous sodium hydroxide solution.

In order to obtain phosgene having a high purity, carbon monoxide and chlorine are reacted with each other while always controlling the mixing ratio of carbon monoxide to chlorine to not less than 1. However, for the purpose of reduction of off-gas (improvement of unit of phosgene), the mixing ratio of carbon monoxide to chlorine is usually adjusted so as to be as close to 1 as possible, so that unreacted chlorine still remains after the reaction. The unreacted chlorine is preferably removed by adsorbing it into activated carbon. Further, in the reaction system, halides such as carbon tetrachloride, chloroform and methylene chloride are present as impurities. These impurities may be removed at a phosgene distillation stage prior to the reaction, or at a next stage where a by-produced gas (hydrogen chloride) obtained upon the reaction of phosgene with the aromatic monohydroxy compound is purified.

Carbon monoxide:

As the method of generating carbon monoxide which is reacted with chlorine for the production of phosgene, there are hitherto known various methods such as coke partial oxidation method, methanol decomposition method, LPG reforming method or the like. However, in any method, the separation of carbon monoxide from carbon dioxide is inevitably required. Further, carbon disulfide and carbonyl sulfide partially mixed in carbon monoxide are converted into hydrogen sulfide using a Claus catalyst. Then, the carbon monoxide gas containing carbon dioxide and hydrogen sulfide is purified by passing through a decarbonation and desulfurization column to remove carbon dioxide and hydrogen sulfide therefrom using sodium hydroxide. A very small amount of residual sulfur compounds may be absorbed and removed using zinc oxide.

In accordance with the present invention, hydrogen chloride by-produced at diaryl carbonate production step is converted into chlorine, and then reused in the production of phosgene. As a result, it is possible to provide an ideal closed-cycle process for the production of diaryl carbonate.

EXAMPLES

The present invention will be described in more detail by reference to the following examples. However, these examples are only illustrative and not intended to limit the present invention thereto.

Example 1:

Respective steps are explained below by referring to FIGS. 1 to 4.

(1) Production of Carbon Monoxide (CO)

Figure 1:
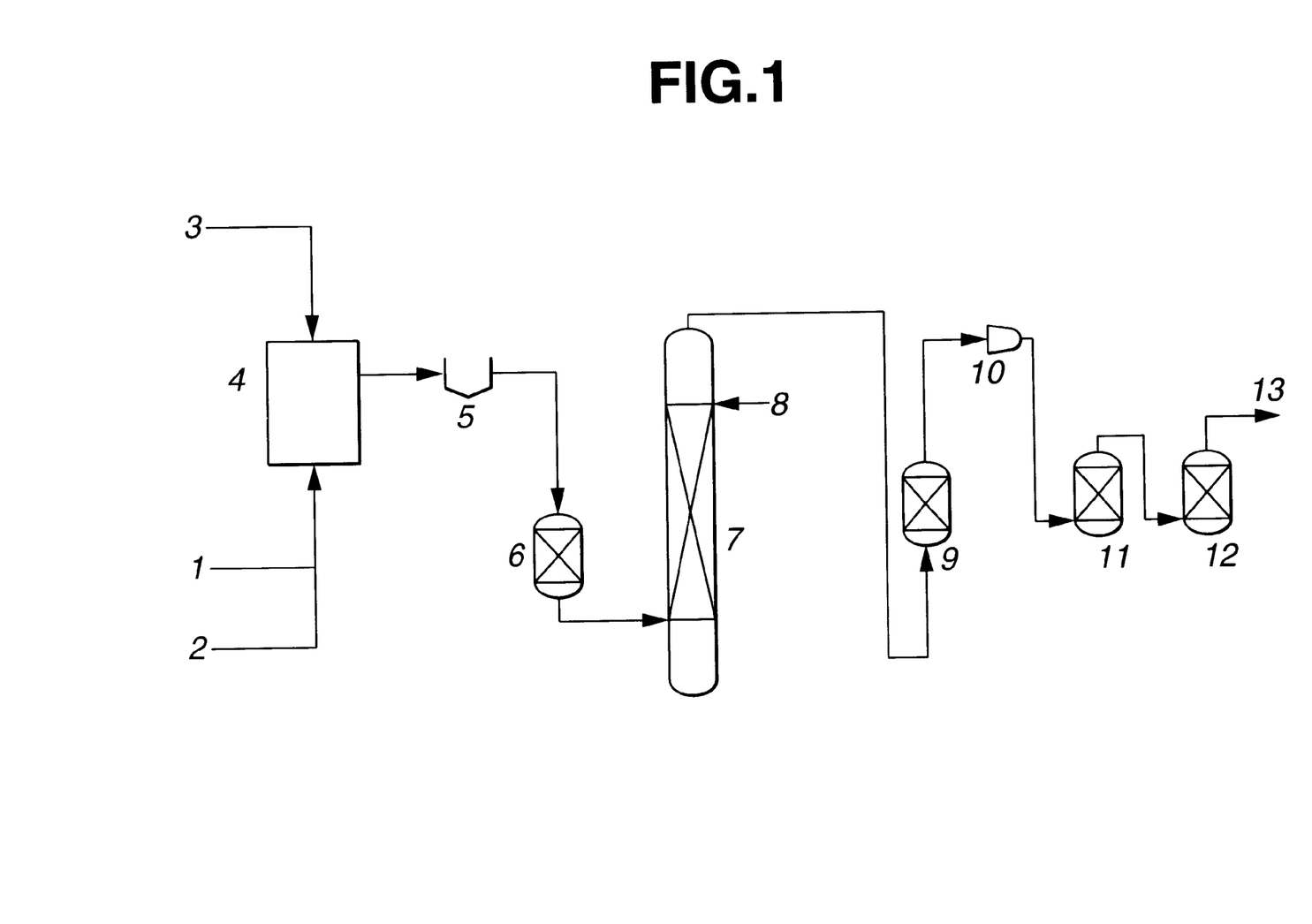
FIGS. 1 to 4 are flow sheets showing whole steps for the production of diaryl carbonate.

The production of carbon monoxide is explained below by referring to FIG. 1.

While supplying a carbon dioxide gas (1) and an oxygen gas (2) both having a temperature of 20° C., into a Co generator (4) at feed rates of 2.06 Nm$^3$/hr and 1.13 Nm$^3$/hr, respectively, coke (3) was burned at a rate of 2.23 kg/hr, thereby obtaining a crude CO gas (carbon monoxide: 65.2 vol. %; carbon dioxide: 27.8 vol. %; water: 7.0 vol. %; hydrogen: trace; carbonyl sulfide (COS): 1,000 ppm; hydrogen sulfide: 500 ppm; carbon disulfide: 100 ppm; dusts) at a flow rate of 5.28 Nm$^3$/hr. The generator (4) heated to a high temperature was cooled with desalted water to adjust the temperature of the product gas to 250° C.

The product gas was pressurized to 3,500 mmAq using a blower, and passed through a filter (5) to remove dusts therefrom. Then, the product gas was supplied to a Claus catalyst column (6) to hydrolyze COS and carbon disulfide contained as impurities therein into hydrogen sulfide, and then air-cooled up to 60° C.

The obtained gas (carbon monoxide: 63.4 vol. %; carbon dioxide: 27.0 vol. %; water: 9.7 vol. %; hydrogen: trace; COS: 10 ppm; hydrogen sulfide: 1,690 ppm) was fed to a decarbonation and desulfurization column (7) where the gas was contacted with an aqueous potassium carbonate solution (8) by counter-flow method to decarbonate and desulfurize the gas. Thereafter, the treated gas was heated to 120° C. and fed to a zinc oxide column (9) in order to remove a very small amount of the residual sulfur compound (COS: 10 ppm) by absorbing the compound into zinc oxide. The adsorption-purified gas was cooled to 40° C., pressurized to 5.0 kg/cm$^2$G by a compressor (10), and passed through a decarbonation column (11) and then a dehydration column (12), thereby obtaining a purified CO gas (13) (carbon monoxide: 96.9 vol. %; hydrogen: 3.1 vol. %; carbon dioxide: trace; water: trace) at a flow rate of 3.55 Nm$^3$/hr.

(2) Production of Phosgene

Figure 2:
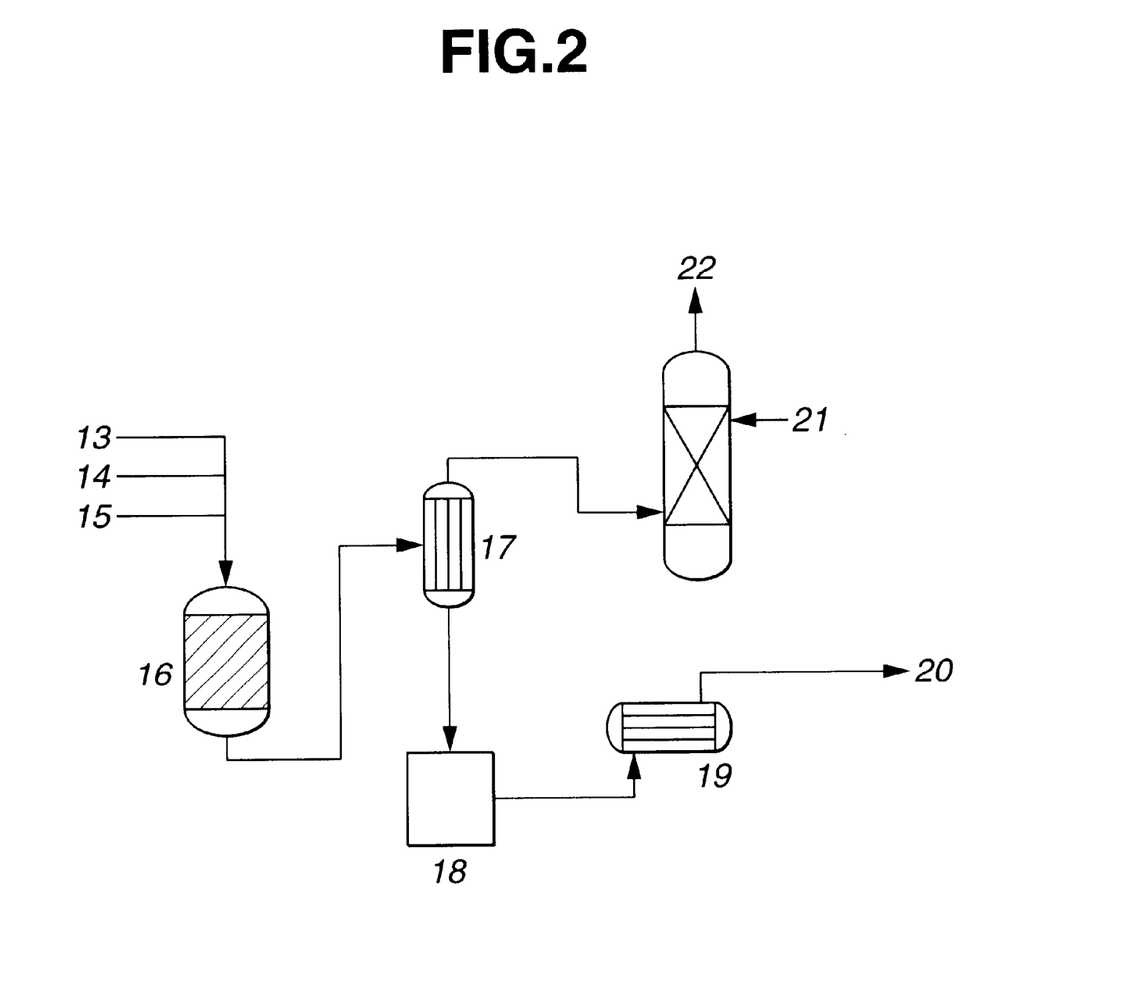

The production of phosgene is explained below by referring to FIG. 2.

The thus obtained purified CO gas (13) and a mixed gas (chlorine: 99.8 vol. %; oxygen: 0.2 vol. %) composed of a recovered chlorine gas (14) recovered from hydrogen chloride described hereinafter and a chlorine gas (15) obtained by an electrolytic soda process, were supplied to a gas mixer (not shown) at feed rates of 3.55 Nm$^3$/hr and 3.33 Nm$^3$/hr, respectively. The thus obtained mixed gas was fed to a phosgene reactor (16) of a shell-and-tube type packed with granular activated carbon and capable of removing the heat of reaction by a coolant. The phosgene production reaction was conducted at 70° C. under a pressure of 3.9 kg/cm$^2$G, thereby obtaining a crude phosgene gas (phosgene: 91.0 vol. %; carbon monoxide: 5.1 vol. %; hydrogen chloride: 1.7 vol. %; hydrogen: 2.0 vol. %; carbon dioxide: 0.2 vol. %) at a flow rate of 3.63 Nm$^3$/hr. The thus obtained crude phosgene gas was introduced into a condenser (17) where the gas was cooled to –5° C. with brine to obtain liquefied phosgene at a flow rate of 14.5 kg/hr. The liquefied phosgene was stored in a storage tank (18). The thus stored liquefied phosgene had a phosgene concentration of not less than 99.7% by weight, and further contained as impurities, 0.3% by weight of hydrogen chloride and a trace amount of carbon tetrachloride. The liquefied phosgene was vaporized at an evaporator (19) and then used as purified phosgene (20) for the production of diphenyl carbonate.

On the other hand, the residual gas (carbon monoxide: 52.3 vol. %; phosgene: 12.1 vol. %; hydrogen chloride: 11.2 vol. %; hydrogen: 22.4 vol. %; carbon dioxide: 1.9 vol. %) discharged from the condenser (17) was fed to a detoxification column through which an aqueous sodium hydroxide solution (21) was circulated. After completely decomposing phosgene contained in the residual gas, the harmless off-gas (22) was discharged from the detoxification column into atmosphere.

(3) Production of Diphenyl Carbonate

Figure 3:
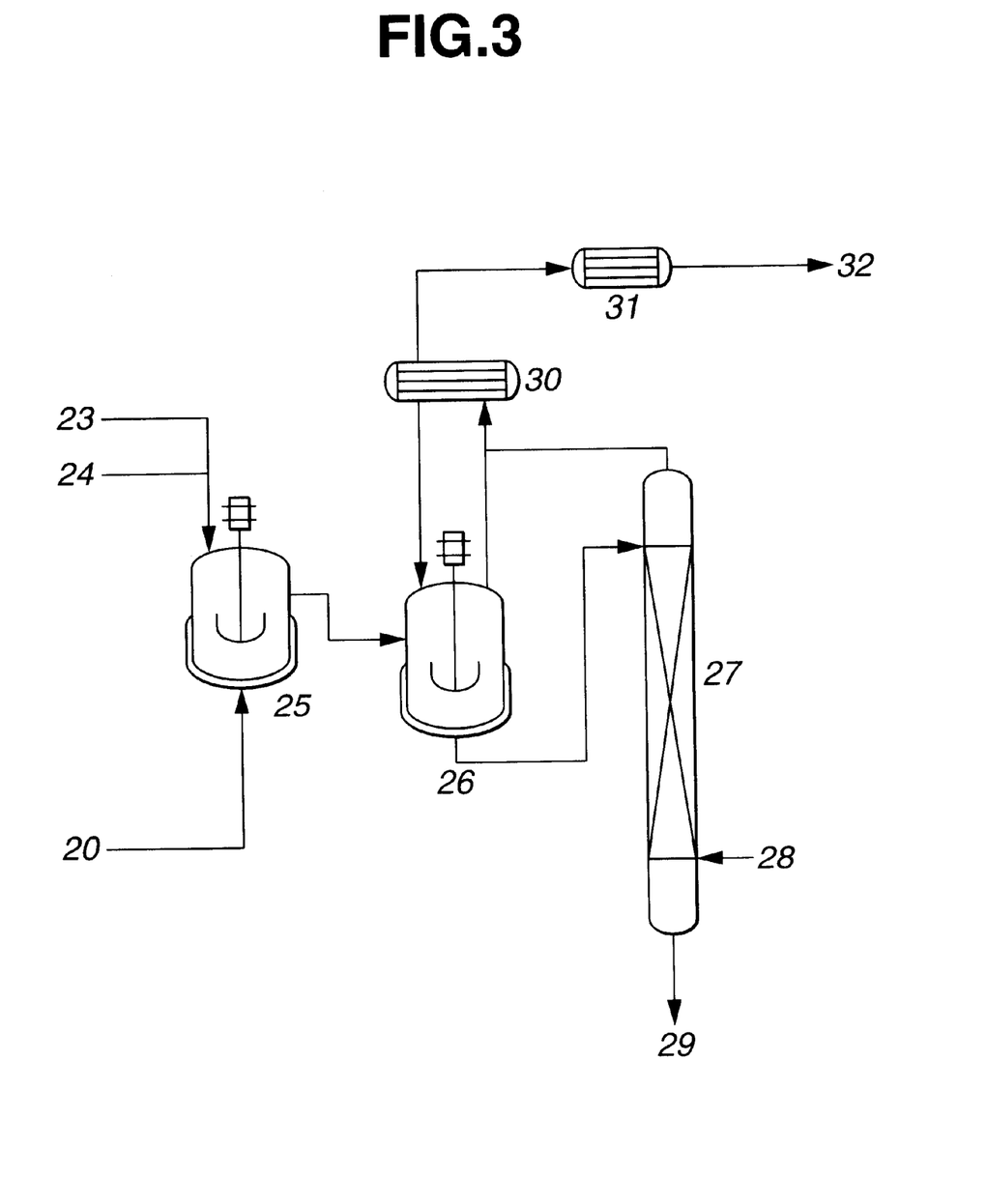

The production of diphenyl carbonate is explained below by referring to FIG. 3.

Molten phenol (23) heated to 50° C. and pyridine (24) as a catalyst were continuously supplied to a first reactor (25) at feed rates of about 30.0 kg/hr (0.319 kmol/hr) and 0.757 kg/hr (0.00957 kmol/hr), respectively, and the resultant mixture was heated to 150° C. therein. While vigorously stirring the contents of the first reactor, the purified phosgene (20) was continuously fed to the first reactor (25) in an amount corresponding to a molar ratio of phosgene to phenol supplied of 0.46 mole (i.e., 3.286 Nm$^3$/hr: 0.1467 kmol/hr). The reaction mixture discharged from the first reactor was fed in the form of a mixed gas/liquid phase through an overflow pipe into a second reactor (26). In the second reactor (26), the temperature of the mixture was controlled to 150° C. while intimately stirring. The obtained reaction solution was then fed to a degassing column (27) where the solution was contacted with a nitrogen gas (28) at 160° C. by counter-flow method in order to complete the reaction between phenyl chloroformate as an intermediate product and phenol. A reaction mixture (29) was obtained from the bottom of the degassing column at a flow rate of 34.9 kg/hr. After allowing the reaction mixture to stand until the composition thereof was sufficiently stabilized, the reaction mixture was analyzed by gas chromatography. As a result, it was confirmed that the amount of diphenyl carbonate produced was 89.9% by weight and, therefore, almost 100% of phosgene supplied was converted into diphenyl carbonate.

On the other hand, the reaction off-gas discharged from the second reactor (26) and the nitrogen-containing off-gas discharged from the degassing column (27) were mixed together, and then fed to a condenser (30) where the mixed gas was cooled with a circulating SK oil maintained at about 40° C. The obtained condensed solution was returned to the second reactor (26), and the uncondensed gas was further cooled to 10° C. with brine. After cooling, a crude hydrogen chloride gas (32) containing 97.87% by weight of hydrogen chloride, 0.04% by weight of phenol, 2.09% by weight of nitrogen and a trace amount of carbon tetrachloride was produced as an off-gas at a flow rate of about 10.59 kg/hr (6.54 Nm³/hr).

(4) Recovery of Chlorine

Figure 4:
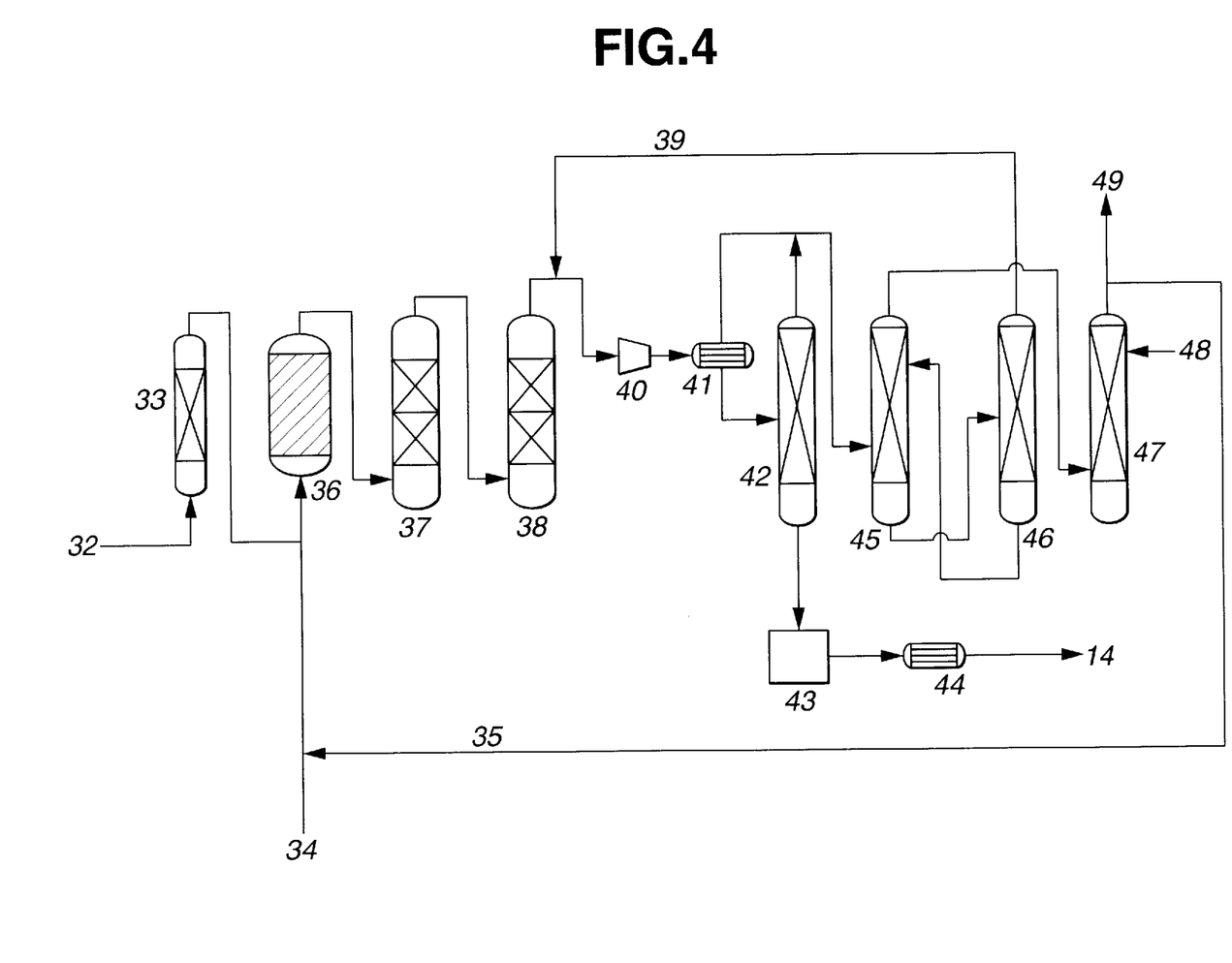

The recovery of chlorine is explained below by referring to FIG. 4.

The above crude hydrogen chloride (32) gas by-produced at the diphenyl carbonate production step was supplied to an activated carbon column (33) packed with granular coal-based activated carbon, at a temperature of 30° C. and a feed rate of 10.59 kg/hr (corresponding to SV=500/hr), thereby adsorbing and removing organic impurities such as phenol and carbon tetrachloride. An oxygen-containing mixed gas composed of an oxygen gas (34) (oxygen: 99.6% by weight; nitrogen: 0.4% by weight) and an oxygen-containing circulating gas (35) (oxygen: 65.9% by weight; nitrogen: 34.1% by weight) discharged from a detoxification column (47) described hereinafter, which were supplied at flow rates of 2.04 kg/hr and 3.81 kg/hr, respectively, was introduced into a heater in such an amount that the amount of oxygen contained in the mixed gas was 0.5 mole based on one mole of hydrogen chloride as the raw material, heated to 200° C. by heated steam, and then fed into a fluidized bed reactor (36).

The fluidized bed reactor (36) was an Ni-clad cylindrical reactor having a diameter of about 0.15 m and a height of about 2 m, and was filled with about 6.5 kg of a chromium oxide catalyst prepared by adding about 10% by weight of silica gel (calculated as $SiO_2$) to a precipitate prepared from chromium nitrate and ammonia water and then calcining the mixture. The oxidation reaction in the fluidized bed reactor (36) was conducted at a temperature of 400° C.

The thus obtained oxidation product gas (chlorine: 42.9% by weight; hydrogen chloride: 18.9% by weight; nitrogen: 9.3% by weight; oxygen: 17.9% by weight; water: 10.9% by weight) was fed to a chromium recovery and hydrogen chloride absorption column (37) composed of a chromium recovery section as the lower part and a hydrogen chloride absorption section as the upper part, at a flow rate of 16.44 kg/hr.

In the chromium recovery section, water was continuously sprayed from a top thereof to wash off hydrogen chloride and vaporized and scattered chromium as a main component of the catalyst in the product gas, and an aqueous chromium solution having a concentration of about 0.8% by weight was continuously taken out from the bottom thereof. After passing through the chromium recovery section, the product gas was fed to the hydrogen chloride absorption section packed with 1-inch Raschig rings. In the absorption section, the product gas was washed with 25° C. water sprayed from a top thereof by counter-flow method. The product gas having a temperature of 60° C. which was water-washed in the absorption section to remove the hydrogen chloride gas therefrom (chlorine: 60.5% by weight; nitrogen: 13.3% by weight; oxygen: 25.7% by weight; water: 0.5% by weight; hydrogen chloride: trace) was cooled to 20° C. by a cooler, and then fed to a sulfuric acid washing column (38) packed with a filler.

In the sulfuric acid washing column (38), a 98% sulfuric acid solution at a flow rate of 0.15 kg/hr together with a circulating sulfuric acid was continuously supplied from a top thereof, and contacted with the product gas by counter-flow method to wash and dehydrate the gas.

The product gas having a temperature of 50° C. which was discharged from the sulfuric acid washing column (38) at a flow rate of 11.44 kg/hr (chlorine: 60.9% by weight; nitrogen: 13.4% by weight; oxygen: 25.8% by weight) was mixed with a chlorine-containing circulating gas (39) discharged from a solvent recovery column (46) described hereinafter, and the resultant mixed gas was fed to a compressor (40) to compress the gas, cooled by a cooler (41), and then supplied to a distillation column (42). In the distillation column, the liquefied chlorine was subjected to distillation, so that impurities contained in the liquefied chlorine were distilled off together with residual gases such as oxygen from a top of the column. The thus purified liquefied chlorine (chlorine: 99.99% by weight; oxygen: 0.01% by weight) was taken out from the bottom of the distillation column into a storage tank (43) at a flow rate of 6.96 kg/hr. The thus stored liquefied chlorine was vaporized and then recycled as the recovered chlorine gas (14) to the phosgene production step.

On the other hand, the unliquefied gas distilled off from the top of the distillation column (chlorine: 42.3% by weight; nitrogen: 19.7% by weight; oxygen: 38.0% by weight) was fed to an absorption column (45) to recover chlorine therefrom. In the absorption column (45), the unliquefied gas was contacted with carbon tetrachloride returned from the solvent recovery column (46) and introduced into the column from a top thereof, by counter-flow method. The carbon tetrachloride solution which was discharged from the absorption column (45) and into which chlorine was absorbed, was fed to the solvent recovery column (46). In the solvent recovery column (46), chlorine was vaporized and recovered at a yield of almost 100%. The chlorine-containing circulating gas (39) discharged from the top of the solvent recovery column (46) was mixed with the product gas discharged from the sulfuric acid washing column (38) as described above. The resultant mixed gas was compressed and cooled, and then supplied to the distillation column (42). The residual gas unabsorbed by carbon tetrachloride and discharged from the top of the absorption column (chlorine: trace; carbon tetrachloride: 0.2% by weight; nitrogen: 34.1% by weight; oxygen: 65.8% by weight) was detoxified with a sodium sulfite solution (48). Then, 85% of the thus treated gas was recycled as the oxygen-containing circulating gas (35) to the fluidized bed reactor for oxidizing the hydrogen chloride gas as described above, and the remainder of the treated gas was discharged as an off-gas (49) into atmosphere.

Example 2

Among the respective steps (1) to (4) of Example 1, only the chlorine recovery step (4) was changed as follows. Namely, the same procedure as defined in Example 1 was conducted except that chlorine was recovered by subjecting the aqueous hydrogen chloride solution to electrolysis, thereby producing diphenyl carbonate.

As a result, it was confirmed that almost 100% of phosgene supplied was consumed, and diphenyl carbonate with a stable predetermined concentration (89.9% by weight) was produced at a flow rate of 34.9 kg/hr.

Figure 5:
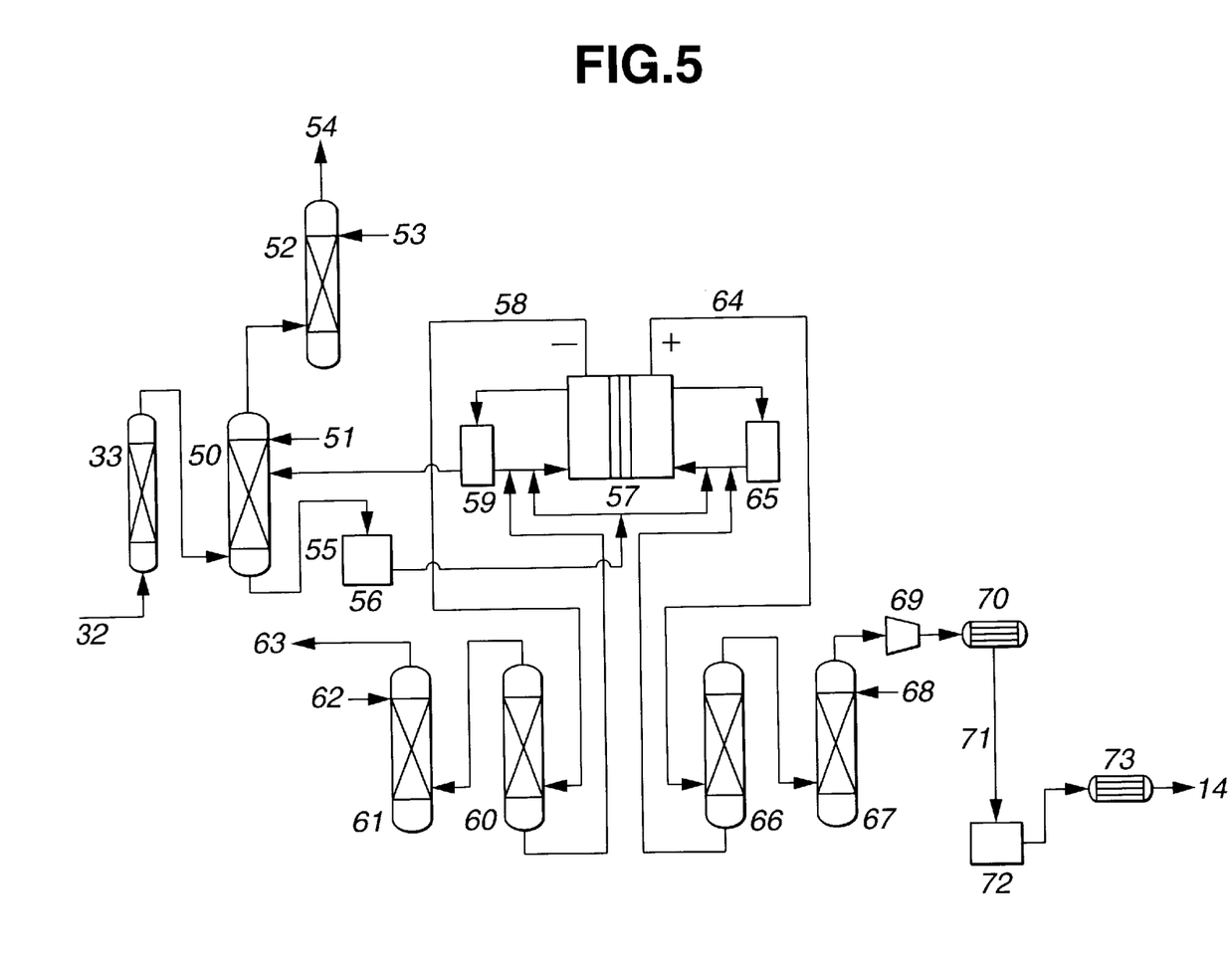
FIGS. 5 to 6 are flow sheets showing respective chlorine recovery steps.

The chlorine recovery step of Example 2 is explained below by referring to FIG. 5.

(4) Chlorine Recovery Step

A crude hydrogen chloride gas by-produced at the diphenyl carbonate production step (hydrogen chloride: 97.87% by weight; phenol: 0.04% by weight; nitrogen: 2.09% by weight; carbon tetrachloride: trace) was supplied to a column packed with granular coal-based activated carbon at a temperature of 30° C. and a feed rate of 10.59 kg/hr (corresponding to SV=500/hr) to adsorb and remove organic impurities such as phenol and carbon tetrachloride therefrom.

After completely removing the organic impurities, the hydrogen chloride gas was fed to an absorption column (50) where hydrogen chloride was absorbed into water (51) supplied from a top thereof and a part of a circulating catholyte (17 wt % hydrochloric acid) supplied from an electrolytic cell and introduced into the column from a mid-position thereof. As a result, a 28 wt % hydrochloric acid solution (hydrogen chloride: 28.0% by weight; water: 72.0% by weight) was obtained at a flow rate of 77.61 kg/hr from the bottom of the absorption column. The gas unabsorbed at the absorption column (50) was fed to a detoxification column (52) where the gas was contacted with an aqueous sodium hydroxide solution (53) by counter-flow method. After the detoxification treatment, the off-gas (54) was discharged into atmosphere.

The 28 wt % hydrochloric acid solution (55) produced at the absorption column (50) was collected into a hydrochloric acid storage tank (56). Thirty-two percent (32%) of the thus collected hydrochloric acid was mixed with condensed water contained in a hydrogen gas (58) produced at the cathode and a part of the circulating catholyte (17 wt % hydrochloric acid) to prepare a 21 wt % hydrochloric acid solution. Then, the 21 wt % hydrochloric acid solution was cooled to 60° C. and then supplied to a cathode chamber (–) of the electrolytic cell (57). The remainder of the 28 wt % hydrochloric acid solution was mixed with condensed water contained in a chlorine gas (64) produced at an anode and a circulating anolyte to prepare a 22 wt % hydrochloric acid solution. Then, the thus prepared 22 wt % hydrochloric acid solution was cooled to 60° C., and then supplied to an anode chamber (+) of the electrolytic cell (57).

The electrolytic cell (57) was divided into the cathode chamber (–) and the anode chamber (+) by a polyvinyl chloride membrane. Graphite electrodes were disposed in the respective chambers. As the electrolytic cell, there was used a bipolar-type electrolytic cell provided with a transformer and a rectifier. The electrolysis was conducted at a temperature of 80° C., a current density of 4.15 kA/m$^2$ and a voltage of 1.95 V.

A crude hydrogen gas (58) generated at the cathode chamber (hydrogen: 15.7% by weight; hydrogen chloride: 3.4% by weight; water: 80.9% by weight) was fed to a cooling column (60), thereby cooling the gas to 410° C. A diluted hydrochloric acid condensed upon the cooling was mixed with the 28 wt % hydrochloric acid solution and the circulating catholyte as described above, and then fed to the cathode chamber (–). The cooled hydrogen gas was fed to a neutralization column (61) where the gas was neutralized with an aqueous sodium hydroxide solution (62) in order to remove hydrogen chloride entrained thereon, thereby obtaining a purified hydrogen gas (63) (hydrogen: 98.5% by weight; water: 1.5% by weight) at a flow rate of 0.29 kg/hr.

A crude chlorine gas (64) generated at the anode chamber (chlorine: 86.7% by weight; hydrogen chloride: 0.5% by weight; water: 12.7% by weight) was fed to a cooling column (66), thereby cooling the gas to 410C. A diluted hydrochloric acid condensed upon the cooling was mixed with the 28 wt % hydrochloric acid solution and the circulating anolyte as described above, and then supplied to the anode chamber (+). The cooled chlorine gas was fed to a drying column (67) through which a concentrated sulfuric acid (68) was circulated, in order to remove water entrained thereon. The dried chlorine gas was sequentially compressed and cooled by a compressor (69) and a condenser (70), respectively. As a result, liquefied and purified chlorine (71) (chlorine: 100.0% by weight) was taken out from the condenser at a flow rate of 10.0 kg/hr and stored in a chlorine storage tank (72). The thus obtained liquefied chlorine was vaporized at an evaporator (73), and then recycled as the recovered chlorine gas (14) to the phosgene production step.

Example 3

Among the respective steps (1) to (4) of Example 1, only the chlorine recovery step (4) was changed as follows. Namely, the same procedure as defined in Example 1 was conducted except that chlorine was recovered by subjecting hydrogen chloride to oxidation reaction using a ruthenium oxide catalyst, thereby producing diphenyl carbonate.

As a result, it was confirmed that almost 100% of phosgene supplied was consumed, and diphenyl carbonate with a stable predetermined concentration (89.9% by weight) was produced at a flow rate of 34.9 kg/hr.

Figure 6:
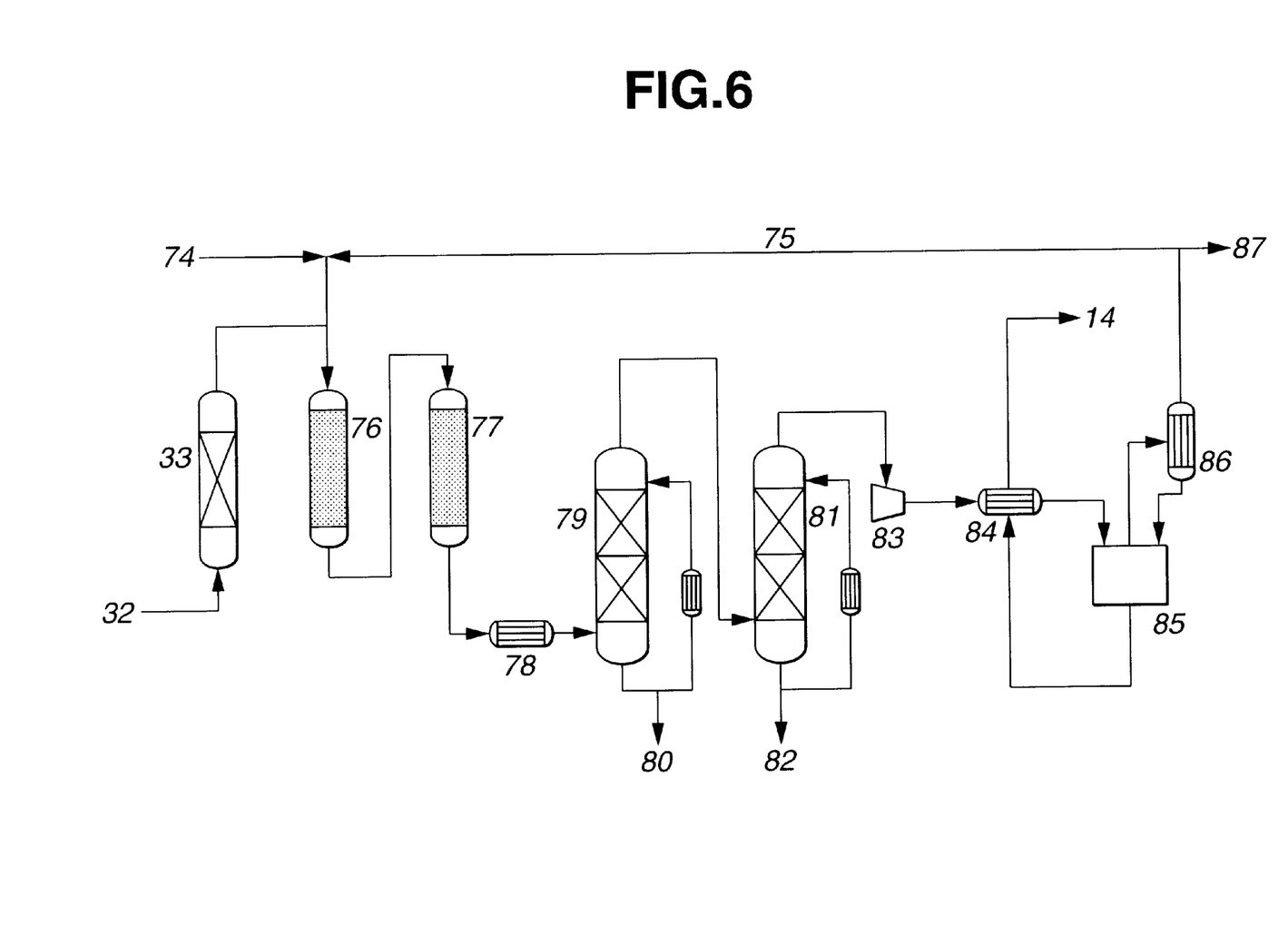

The chlorine recovery step of Example 3 is explained below by referring to FIG. 6.

(4) Chlorine Recovery Step

A crude hydrogen chloride gas by-produced at the diphenyl carbonate production step (hydrogen chloride: 97.87% by weight; phenol: 0.04% by weight; nitrogen: 2.09% by weight; carbon tetrachloride: trace) was supplied to a column packed with granular coal-based activated carbon at a temperature of 30° C. and a feed rate of 10.59 kg/hr (corresponding to SV=500/hr) to adsorb and remove organic impurities such as phenol and carbon tetrachloride therefrom.

A purified hydrogen chloride gas from which organic impurities were completely removed, was mixed with an oxygen-containing mixed gas composed of an oxygen gas (74) (oxygen: 99.6% by weight; nitrogen: 0.4% by weight) supplied at a flow rate of 2.27 kg/hr and an oxygen-containing circulating gas (75) described hereinafter, and then fed to a continuous two-stage reactor constituted by two fixed bed reactors (76) and (77).

Each of the fixed bed reactors was of a Ni-clad shell-and-tube type packed with a titanium oxide-supported ruthenium oxide catalyst prepared by the following method. That is, a mixed solution composed of an aqueous ruthenium chloride solution and an aqueous sodium hydroxide solution was dropped into a water suspension prepared by suspending in water, a white precipitate obtained by pouring an aqueous urea solution into an aqueous titanium tetrachloride solution and heating the resultant mixed solution. Nitric acid was then added to the resultant mixture to prepare a black precipitate. The obtained black precipitate was washed, filtered out and then calcined, thereby obtaining particles. The thus obtained particles were molded to produce the titanium oxide-supported ruthenium oxide catalyst.

The oxidation reaction was conducted under a pressure of 0.8 atm at temperatures of 370° C. in the first stage reactor (76) and 280° C. in the second stage reactor (77).

The oxidation product gas obtained by the oxidation reaction of hydrogen chloride in which about 95% of hydrogen chloride had been converted, was fed to a hydrogen chloride absorption column (79) through a heat exchanger (78). In the hydrogen chloride absorption column (79), unreacted hydrogen chloride and produced water contained in the product gas were removed by water-washing, so that about 17% hydrochloric acid aqueous solution (80) was recovered from the bottom of the absorption column. The gas discharged from a top of the absorption column was fed to a dehydration column (81) where the gas was contacted with a 98% sulfuric acid (82) by counter-flow method to wash and dehydrate the gas.

After the dehydration, the product gas (mixed gas of chlorine, oxygen and nitrogen) was fed to a compressor (83) and cooled to −35° C., thereby obtaining liquefied chlorine at a flow rate 9.78 kg/hr. The thus obtained liquefied chlorine was vaporized by a heat exchanger (84) and then recycled as the recovered chlorine gas (14) to the phosgene production step. On the other hand, unliquefied gas was fed through a storage tank (85) and condensed by a condenser (86). Thereafter, a part of the unliquefied gas was neutralized and then discharged as an off-gas (87) into atmosphere, and the remainder thereof was recycled to the oxidation reaction.

What is claimed is:

1. A process for producing diaryl carbonate, comprising steps of:
   (1) a diaryl carbonate production step of subjecting an aromatic monohydroxy compound and phosgene to condensation reaction at a temperature of 80 to 180° C. in the presence of an aromatic nitrogen-containing heterocyclic compound catalyst to obtain the diaryl carbonate;
   (2) a purification step of removing impurities from a hydrogen chloride gas by-produced upon the condensation reaction;
   (3) a chlorine recovery step of recovering chlorine usable for the production of phosgene from the purified hydrogen chloride gas; and
   (4) a phosgene production step of reacting the recovered chlorine with carbon monoxide to obtain phosgene usable in the diaryl carbonate production step.

2. A process according to claim 1, wherein in said chlorine recovery step, the hydrogen chloride gas is subjected to oxidation reaction using oxygen at a temperature of 200 to 400° C. in the presence of a ruthenium oxide catalyst under such a condition that the oxygen is used in an amount of not less than 0.25 mole based on one mole of the hydrogen chloride.

3. A process according to claim 2, wherein after removing hydrogen chloride and water from a crude chlorine gas obtained by the oxidation reaction, the resultant chlorine gas is compressed and liquefied to obtain chlorine usable in the phosgene production step, and a part of the unliquefied oxygen-containing gas is discharged as an off-gas, and the remainder of the unliquefied oxygen-containing gas is recycled to the oxidation reaction.

4. A process according to claim 1, wherein in said chlorine recovery step, the hydrogen chloride gas is subjected to oxidation reaction using oxygen at a temperature of 300 to 500° C. in the presence of a chromium oxide catalyst under such a condition that the oxygen is used in an amount of not less than 0.25 mole based on one mole of the hydrogen chloride.

5. A process according to claim 4, wherein after removing hydrogen chloride and water from a crude chlorine gas obtained by the oxidation reaction, the resultant chlorine gas is compressed and liquefied to obtain chlorine usable in the phosgene production step, and after recovering chlorine from unliquefied chlorine gas, the recovered chlorine is recycled to said compression and liquefaction step.

6. A process according to claim 5, wherein a part of an oxygen-containing gas obtained after removing chlorine from the unliquefied gas, is discharged as an off-gas, and the remainder of the oxygen-containing gas is recycled to the oxidation reaction.

7. A process according to claim 1, wherein in said chlorine recovery step, the purified hydrogen chloride gas is absorbed into water to prepare an aqueous hydrogen chloride solution having a predetermined concentration, and the aqueous hydrogen chloride solution is subjected to electrolysis.

8. A process according to claim 7, wherein after removing water from a crude chlorine gas obtained by the electrolysis, the resultant chlorine gas is compressed and liquefied to obtain chlorine usable in the phosgene production step, whereupon a part of a circulating catholyte in an electrolytic cell is used to absorb the purified hydrogen chloride gas thereinto.

9. A process according to any one of claims 1 to 8, wherein in said phosgene production step, a crude phosgene gas obtained by reacting chlorine with carbon monoxide is cooled and liquefied to obtain phosgene usable in the diaryl carbonate production step, and the unliguefied gas is discharged as an off-gas after completely removing phosgene therefrom.

* * * * *